(12) United States Patent
Basadonna et al.

(10) Patent No.: US 10,687,698 B2
(45) Date of Patent: Jun. 23, 2020

(54) DIRECT ENDOLUMINAL- AND/OR ENDOVASCULAR-ILLUMINATION SYSTEMS AND METHODS OF USE THEREOF

(71) Applicant: EnlightenVue LLC, Denver, CO (US)

(72) Inventors: Giacomo Basadonna, Haddam, CT (US); Alan Lucas, Brookline, MA (US)

(73) Assignee: EnlightenVue LLC, Denver, CO (US)

( * ) Notice: Subject to any disclaimer, the term of this patent is extended or adjusted under 35 U.S.C. 154(b) by 0 days.

(21) Appl. No.: 16/276,295

(22) Filed: Feb. 14, 2019

(65) Prior Publication Data

US 2020/0077876 A1 Mar. 12, 2020

Related U.S. Application Data

(60) Provisional application No. 62/730,450, filed on Sep. 12, 2018.

(51) Int. Cl.
*A61B 1/00* (2006.01)
*A61B 1/015* (2006.01)
*A61B 1/018* (2006.01)
*A61B 1/06* (2006.01)
(Continued)

(52) U.S. Cl.
CPC ........ *A61B 1/0676* (2013.01); *A61B 1/00082* (2013.01); *A61B 1/015* (2013.01); *A61B 1/018* (2013.01); *A61B 1/05* (2013.01); *A61B 1/00103* (2013.01); *A61B 1/00135* (2013.01); *A61B 1/3137* (2013.01)

(58) Field of Classification Search
CPC ..... A61B 1/00082; A61B 1/015; A61B 1/018; A61B 1/05; A61B 1/3137; A61B 1/32
See application file for complete search history.

(56) References Cited

U.S. PATENT DOCUMENTS 4,470,407 A * 9/1984 Hussein ............. A61B 1/00082
600/108
5,025,778 A 6/1991 Silverstein
(Continued)

FOREIGN PATENT DOCUMENTS

WO WO 2013/064060 5/2013

OTHER PUBLICATIONS

International Search Report and Written Opinion dated Nov. 18, 2016 in Application No. PCT/US2016/045417.
(Continued)

*Primary Examiner* — John P Leubecker
(74) *Attorney, Agent, or Firm* — Knobbe Martens Olson & Bear LLP

(57) ABSTRACT

In some embodiments, endoscopy systems and/or methods of using endoscopy systems are described. In some embodiments, an endoscopy system comprises a shaft having an image sensor within a distal tip of the shaft. The shaft can have an expandable cuff disposed on an outer surface of the shaft. The expandable cuff can be moved from a contracted configuration to a deployed configuration. In the deployed configuration, an outer surface of the expandable cuff can inhibit, reduce, or prevent fluid (e.g., blood) flow in the vessel. Inhibiting or preventing the fluid flow can permit direct visualization of the interior of the vessel by the image sensor without interference from the fluid.

13 Claims, 8 Drawing Sheets

(51) Int. Cl.
*A61B 1/05* (2006.01)
*A61B 1/313* (2006.01)

(56) References Cited

U.S. PATENT DOCUMENTS

| | | | | |
|---|---|---|---|---|
| 5,090,959 | A * | 2/1992 | Samson | A61M 25/104 |
| | | | | 600/116 |
| 5,263,928 | A * | 11/1993 | Trauthen | A61M 25/01 |
| | | | | 600/129 |
| 5,464,394 | A * | 11/1995 | Miller | A61M 25/005 |
| | | | | 604/103.1 |
| 5,810,776 | A | 9/1998 | Bacich et al. | |
| 2002/0028986 | A1 * | 3/2002 | Thompson | A61B 1/0669 |
| | | | | 600/178 |
| 2003/0065318 | A1 | 4/2003 | Pendekanti | |
| 2003/0088210 | A1 * | 5/2003 | Miskolczi | A61B 1/00039 |
| | | | | 604/99.02 |
| 2004/0003819 | A1 * | 1/2004 | St. Goar | A61B 17/00234 |
| | | | | 128/898 |
| 2004/0097788 | A1 * | 5/2004 | Mourlas | A61B 1/00082 |
| | | | | 600/116 |
| 2005/0075711 | A1 | 4/2005 | Neary | |
| 2005/0272975 | A1 | 12/2005 | McWeeney et al. | |
| 2006/0064059 | A1 * | 3/2006 | Gelfand | A61B 5/02028 |
| | | | | 604/103.06 |
| 2006/0184048 | A1 * | 8/2006 | Saadat | A61B 1/0008 |
| | | | | 600/478 |
| 2008/0058836 | A1 * | 3/2008 | Moll | A61B 1/00082 |
| | | | | 606/130 |
| 2009/0076331 | A1 | 3/2009 | Konwitz | |
| 2010/0063358 | A1 | 3/2010 | Kessler | |
| 2011/0054326 | A1 * | 3/2011 | Barnett | A61B 1/00087 |
| | | | | 600/453 |
| 2011/0092766 | A1 | 4/2011 | Monassevitch et al. | |
| 2011/0184233 | A1 | 7/2011 | Fructus | |
| 2014/0039253 | A1 * | 2/2014 | Fang | A61B 1/042 |
| | | | | 600/103 |
| 2014/0249569 | A1 | 9/2014 | Kusleika | |
| 2014/0378771 | A1 | 12/2014 | St. Onge et al. | |
| 2015/0065794 | A1 | 3/2015 | Knight | |
| 2015/0150442 | A1 * | 6/2015 | Tafti | A61B 1/00082 |
| | | | | 600/108 |
| 2016/0144155 | A1 * | 5/2016 | Simpson | A61B 1/00082 |
| | | | | 600/427 |
| 2017/0027458 | A1 * | 2/2017 | Glover | A61B 5/028 |
| 2017/0035277 | A1 * | 2/2017 | Kucharski | A61B 1/018 |
| 2017/0245737 | A1 | 8/2017 | Truckai et al. | |
| 2018/0084971 | A1 | 3/2018 | Truckai et al. | |
| 2018/0160893 | A1 | 6/2018 | Truckai et al. | |
| 2018/0184892 | A1 | 7/2018 | Truckai et al. | |
| 2018/0249888 | A1 | 9/2018 | Kucharski et al. | |
| 2018/0326144 | A1 | 11/2018 | Truckai et al. | |

OTHER PUBLICATIONS

International Search Report dated Nov. 18, 2019 in related International Application No. PCT/US2019/050760.

* cited by examiner

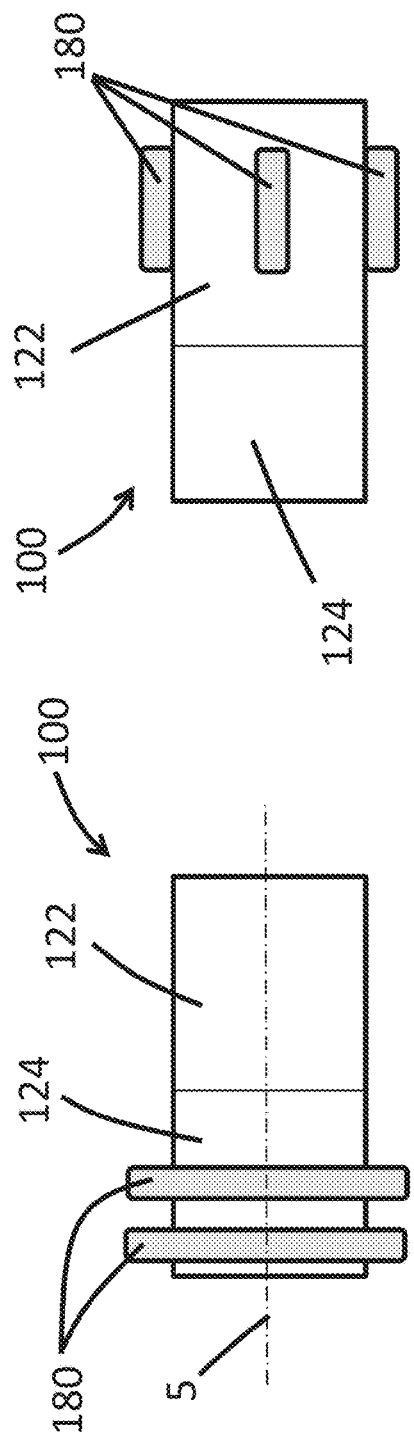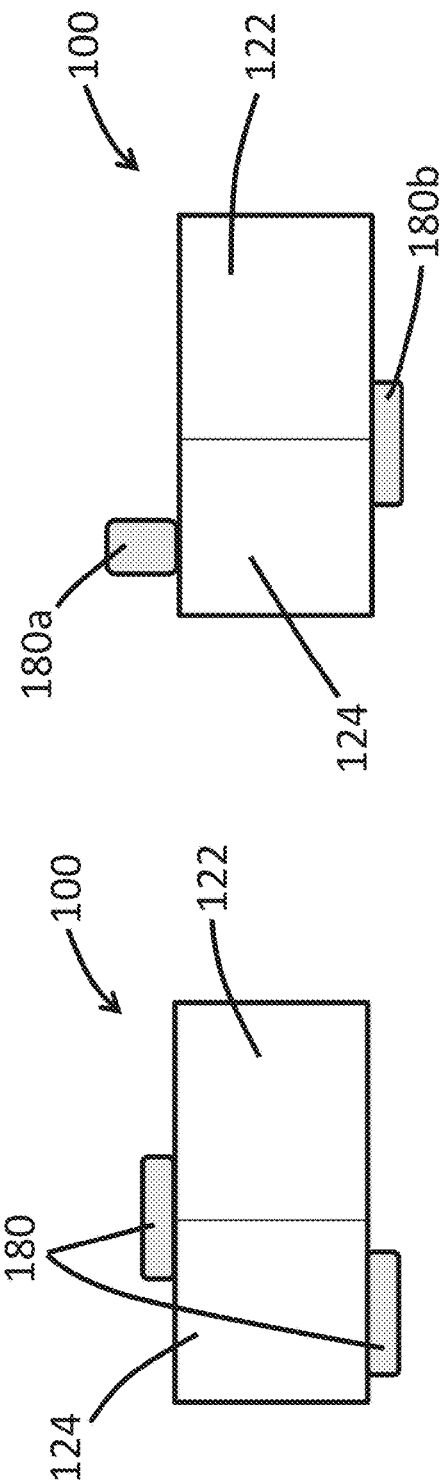
FIG. 3A  FIG. 3B  FIG. 3C  FIG. 3D

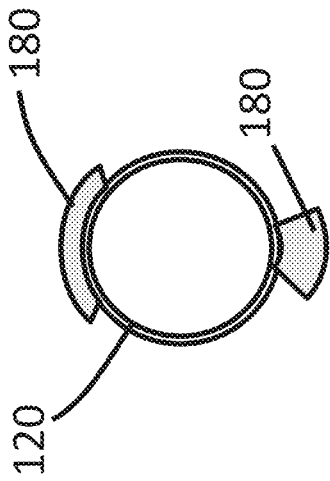
FIG. 4A
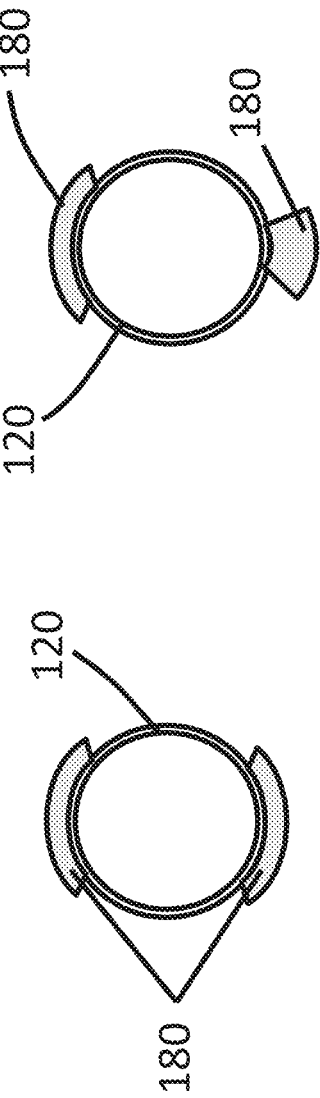
FIG. 4B
FIG. 4C
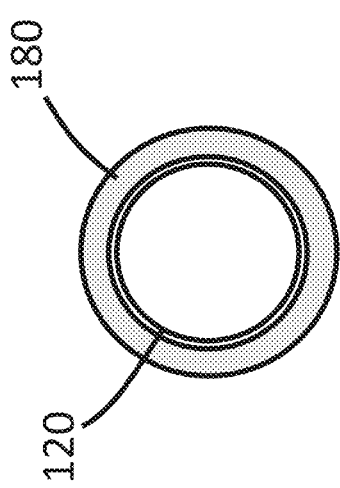
FIG. 4D
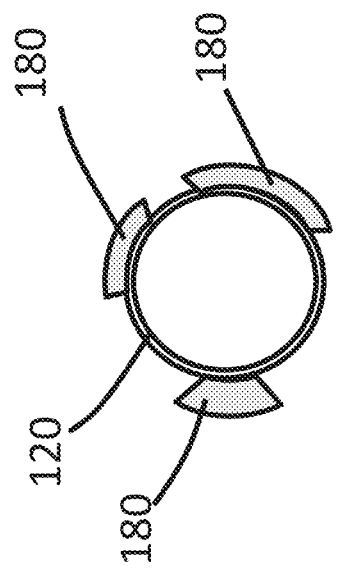
FIG. 4E

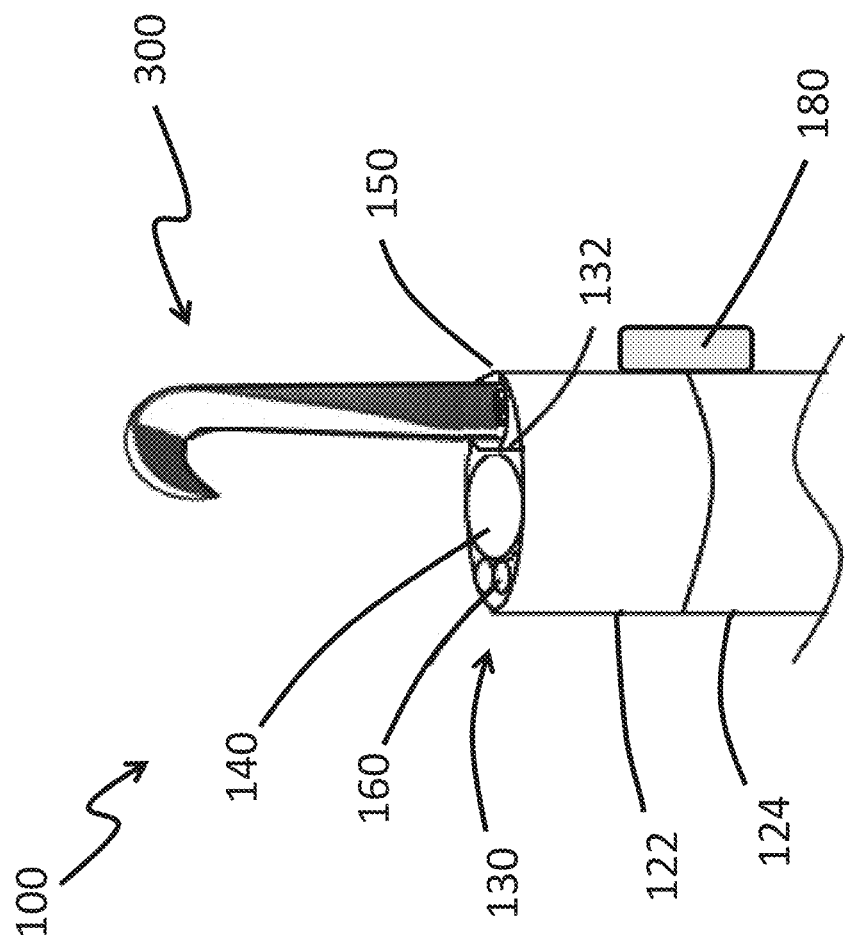

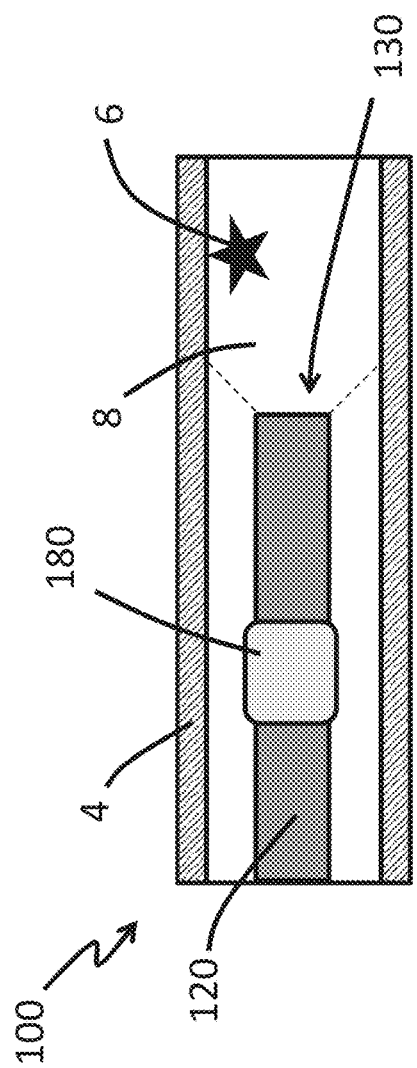
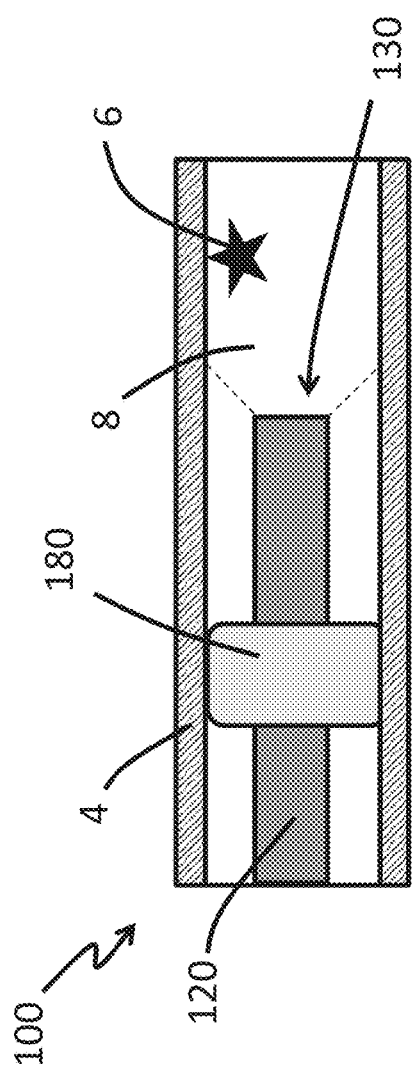

DIRECT ENDOLUMINAL- AND/OR ENDOVASCULAR-ILLUMINATION SYSTEMS AND METHODS OF USE THEREOF

INCORPORATION BY REFERENCE

This application claims the benefit of U.S. Provisional Application No. 62/730,450, filed Sep. 12, 2018, which is hereby incorporated by reference in its entirety. This application incorporates by reference the entirety of International Application No. PCT/US2016/045417 designating the United States, filed on Aug. 3, 2016. The International Application was published in English as WO 2017/027299 A1 on Feb. 16, 2017. The priority US Application of the International Application, U.S. application Ser. No. 14/821,579, filed Aug. 7, 2015, published as US Pub. No. 2017/0035277 on Feb. 9, 2017, is also incorporated by reference in its entirety.

BACKGROUND

Endoscopes, for example microendoscopes, can be used for imaging and/or to perform minimally-invasive procedures (e.g., surgery). Endoscopes can comprise, consist essentially of, or consist of a catheter-based device, and can be designed to permit a health care practitioner such as a physician to visualize and/or treat the internal tissues of a patient through a small incision in the skin. An endoscope can include a light source and a camera. Some endoscopes (which may be referred to as fiberscopes or fiber-optic endoscopes) can include illumination fibers or light guides that direct light to illuminate the field of view.

FIELD

The present disclosure relates to endoscopes and endoscopy systems. More particularly, some embodiments herein relate to methods and endoscopy systems comprising radially-expandable features. The radially-expandable features can inhibit, reduce, or prevent fluid flow inside a vessel such as a blood vessel, permitting direct imaging of the inside of the vessel. In some embodiments, the endoscopy systems are useful for direct visualization of endovascular lumens (without interference from fluid such as blood). In some embodiments, the endoscopy systems are useful for orthopedic procedures. In some embodiments, the endoscopy systems are useful for arthroscopic procedures.

SUMMARY

Some embodiments include an endoscope comprising a hub, and a shaft extending from the hub, the shaft having a distal tip. An image sensor disposed within the distal tip has a field of view external from the endoscope. An illuminating element within the distal tip emits light within the field of view of the image sensor. An expandable cuff (such as a radially expandable cuff) disposed on at least a portion of the shaft is moveable between a contracted configuration and a deployed configuration. An outer surface of the expandable cuff is disposed further away from a longitudinal axis of the shaft when the expandable cuff is in the deployed configuration than when the expandable cuff is in the contracted configuration. In some embodiments, the endoscope is configured for use in a specified vessel (e.g., a blood vessel or chamber of the heart), and the expandable cuff, when deployed, in combination with the shaft, occupies all or substantially all of an interior area of a cross section of the vessel. As such, when deployed, the expandable cuff and shaft can inhibit, reduce, or prevent fluid flow (e.g., blood flow) in the vessel. For example, preventing blood flow can stop the blood flow. In some embodiments, the deployed expandable cuff, in combination with the shaft, occupies at least 80%, 85%, 90%, 91%, 92%, 93%, 94%, 95%, 96%, 97%, 98%, 99%, 99.5%, 99.9%, or 100% of the interior area of the cross section of the vessel. In some embodiments, the endoscope is configured for use in the specified vessel, and the expandable cuff, when deployed, has an outer diameter that is the same or about the same as an inner diameter of the specified vessel. In some embodiments, the endoscope is configured for use in the specified vessel, and the expandable cuff, when deployed, has an outer diameter that is within 20%, 15%, 10%, 5%, 4%, 3%, 2%, or 1% of the inner diameter of the specified vessel. In some embodiments, the deployed expandable cuff is configured to exert a radially-outward force on an inside surface of the specified vessel. In some embodiments, the expandable cuff is an anchoring sleeve. In some embodiments, the expandable cuff includes a lumen in fluid communication with the hub. In some embodiments, the expandable cuff moves from the contracted configuration to the deployed configuration when a fluid or gas is introduced into the lumen through the inflation port as described herein. In some embodiments, the endoscope is configured for use in a specified vessel, in which the expandable cuff, when deployed, has an outer diameter that is about the same or within 20%, 15%, 10%, 5%, 4%, 3%, 2%, or 1% of the inner diameter of the specified vessel. In some embodiments, when the expandable cuff is deployed, the endoscope has an outer diameter sufficient to inhibit, reduce, or prevent fluid flow (such as blood flow) in the specified vessel. In some embodiments, the endoscope is configured for percutaneous access to the specified vessel. In some embodiments, the endoscope is configured for use in a specified vessel selected from the group consisting of: a femoral artery, a radial artery, a coronary artery, a carotid artery, an aorta, and a pulmonary vein such as the inferior vena cava, a peripheral vein or two or more of the listed items. As such, in some embodiments, the endoscope is configured to exert a radially-outward force via the expandable cuff on an inside surface of a vessel selected from the group consisting of: a femoral artery, a radial artery, a coronary artery, a carotid artery, an aorta, and a pulmonary vein such as the inferior vena cava, a peripheral vein or two or more of the listed items. The deployed expandable cuff can temporarily inhibit, decrease, or prevent blood flow in the vessel, permitting a direct visualization of inside aspects of the vessel. The visualization can be performed by the image sensor. In some embodiments, the endoscope is configured for percutaneous access to an occlusion in a peripheral vessel, such as a leg, foot, ankle, arm, or hand, for example in a diabetic or vasculopathic patient. Frequently, such occluded peripheral vessels are arteries, though use in other peripheral vessels such as veins is also contemplated. As such, the endoscope can be used for direct imaging and procedures for treating peripheral vascular disease. In some embodiments, the expandable cuff (as disposed on the shaft of the endoscope), when deployed, is configured to inhibit, reduce, or stop fluid flow in the vessel (for example, blood flow in a blood vessel). As such, the endoscope can be configured for directly imaging the interior of the vessel (e.g., without interference from fluid such as blood). In some embodiments, the target location comprises a peripheral artery, and the vessel is the peripheral artery. In some embodiments, the endoscope is configured to access the foot via the femoral artery, for example for treatment of an extremity vascular occlusion in a diabetic patient. In some embodiments, the endoscope is configured to access the brain via the radial artery (it is contemplated that such an endoscope will have a suitable length to reach the brain via the radial artery), for example to deliver an instrument or perform imaging or a surgical procedure in the brain. In some embodiments, the expandable cuff includes two or more portions circumferentially disposed around the shaft. In some embodiments, the endoscope further comprises a working channel disposed within the shaft and extending from the hub to the distal tip. At least a portion of the working channel is disposed between the longitudinal axis of the shaft and an overlying portion of the expandable cuff. In some embodiments, the overlying portion of the expandable cuff comprises an inner surface disposed between the working channel and an internal space of the expandable cuff, with the inner surface being less distensible than the outer surface. In some embodiments, the internal space of the expandable cuff includes a plurality of inflation channels with each of the plurality of inflation channels being fluidically isolated from one another. In some embodiments, the expandable cuff has a longitudinal length of at least about 2 centimeters, for example less than about 2, 1.5, 1, 0.5, 0.2, or 0.1 centimeters. In some embodiments, the endoscope includes a mitral clip, and the endoscope is configured for use in the inferior vena cava. In some embodiments, the endoscope includes a mitral clip, and the endoscope is configured to deploy the mitral clip in the heart percutaneously. In some embodiments the endoscope is for vascular access to the heart, for example via the inferior vena cava. Advantageously, trans-vascular access to the heart (such as via the superior vena cava) can facilitate direct visualization of the target tissue. Accordingly, in accordance with some embodiments, the endoscope is configured for deployment of the expandable cuff in the inferior vena cava so that the outer diameter is about the same or within 20% of the inner diameter of the inferior vena cava, thus inhibiting, or stopping blood flow in the inferior vena cava. In some embodiments, the endoscope is configured to exert a radially-outward force on an inside surface of the inferior vena cava. In some embodiments, the deployed cuff immobilizes the endoscope in the inferior vena cava. In some embodiments, the method of deploying a mitral clip in the heart comprises advancing the endoscope through the heart, deploying the expandable cuff in the inferior vena cava (so that the endoscope is immobilized in the inferior vena cava), visualizing the target tissue with the image sensor of the endoscope, and deploying the mitral clip. It is contemplated that in some embodiments, advancing the endoscope through the aorta and/or via a puncture of the heart apex (instead of trans-vascularly) can also be used to access the heart and deploy the mitral clips. In some embodiments, the endoscope is configured to ablate the pulmonary vein using electrocautery or cryotherapy. In some embodiments, the target tissue is visualized in the absence of blood flow. The endoscope comprising the expandable cuff in the deployed configuration can inhibit, reduce, or stop the blood flow so as to permit the visualization. In some embodiments, the endoscope is a microendoscope.

Some embodiments include a method of imaging an interior of a vessel (for example a blood vessel or chamber of the heart). The method can comprise advancing an endoscope within a vessel to a target location. The endoscope can be an endoscope comprising an expandable cuff as described herein. In some embodiments, the endoscope comprises a hub, a shaft extending from the hub and comprising a distal tip, an image sensor within the distal tip, the image sensor having a field of view external from the endoscope, and an expandable cuff disposed on at least a portion of the shaft, the expandable cuff being movable between a contracted configuration and a deployed configuration. An outer surface of the expandable cuff can be disposed further away from a longitudinal axis of the shaft when the expandable cuff is in the deployed configuration than when the expandable cuff is in the contracted configuration. The method can comprise expanding the expandable cuff of the endoscope so that the expandable cuff and at least the portion of the shaft occupy all or substantially all of an interior area of a cross section of the vessel, so that fluid flow in the vessel is inhibited, reduced, or prevented. The method can comprise collecting an image of the interior of the vessel at the target location while the fluid flow is inhibited, in which the image is sensed by the image sensor. In some embodiments, inhibiting, reducing, or preventing fluid flow in the vessel is effective to permit visualization of the interior of the vessel. In some embodiments, the deployed expandable cuff, in combination with the shaft, occupies at least 80%, 85%, 90%, 91%, 92%, 93%, 94%, 95%, 96%, 97%, 98%, 99%, 99.5%, 99.9%, or 100% of the interior area of the cross section of the vessel. In some embodiments, the endoscope is configured for use in the specified vessel, and the expandable cuff, when expanded, has an outer diameter that is the same or about the same as an inner diameter of the specified vessel. In some embodiment, expanding the expandable cuff comprises introducing a fluid into an internal space of the expandable cuff. In some embodiments, the vessel is selected from the group consisting of the femoral artery, radial artery, superior vena cava, aorta, and pulmonary vein. In some embodiments, the target location comprises a peripheral artery, and wherein the vessel is the peripheral artery. In some embodiments, the target location is selected from the group consisting of a heart, a brain, a leg, a foot, an ankle, an arm, or a hand. In some embodiments, the method comprises percutaneous advancing the endoscope to the vessel and target area. In some embodiments, the endoscope further comprises a working channel, and the method further comprises deploying an instrument from the working channel of the endoscope. At least a portion of the working channel can pass between the expandable cuff and a longitudinal axis of the endoscope. In some embodiments, deploying the instrument comprises distending an inner surface of the expandable cuff with an outer surface of the working channel. In some embodiments, the instrument comprises a mitral clip. The vessel can be selected from the group consisting of the inferior vena cava and the aorta. In some embodiments, the target location comprises the heart, and the vessel is the inferior vena cava, and the method further comprises visualizing tissue of the heart while the expandable cuff is expanded in the inferior vena cava. The mitral clip can be applied to the heart after the visualizing. In some embodiments, the instrument ablates a portion of a pulmonary vein. In some embodiments, the endoscope further comprises an illuminating element within the distal tip. The illuminating element can be configured to emit light within a field of view of the image sensor. The method can further comprise illuminating the interior of the vessel at the target location with the illuminating element. In some embodiments, advancing comprises moving the endoscope along a guidewire toward the target location. In some embodiments, advancing further comprises halting the endoscope along the guidewire, and expanding the expandable cuff (so that the expanded expandable cuff and shaft inhibit, reduce, or prevent blood flow in the vessel), and imaging (via the image sensor) a field of view in the vessel while the blood flow is inhibited, reduced, or prevented. The method can further comprise contracting the expandable cuff, and resuming moving the endoscope toward the target location along the guidewire. In some embodiments, the vessel is the radial artery or femoral artery. In some embodiments, the vessel is the coronary artery, and the target location comprises a portion of the coronary artery comprising an obstruction. In some embodiments, the method further comprises removing fluid and/or tissue from the interior of the vessel prior to imaging. For example, fluid and/or tissue can be aspirated through one or more working channels of the endoscope as described herein. For example, the vessel can be flushed prior to imaging.

Some embodiments include an endoscopy system comprising an endoscope as described herein, a guidewire, and an inflation pump. In some embodiments, the endoscope comprises an image sensor disposed within a distal tip of the endoscope. In some embodiments, the endoscope further comprises an illuminating element disposed within the distal tip and an expandable cuff disposed on an outer surface of the endoscope. The guidewire can be sized to pass through a lumen of the endoscope. The inflation pump can be in fluid communication with an internal space of the expandable cuff.

BRIEF DESCRIPTION OF THE DRAWINGS

FIGS. 3A-3D is a side view of a distal tip of an endoscope comprising an expandable cuff in accordance with some embodiments herein.

FIGS. 4A-4E is an end view of a distal tip of an endoscope comprising an expandable cuff in accordance with some embodiments herein.

FIG. 5 is a schematic diagram of an endoscopy system comprising a tool adapted to extend past a distal end of the working channel in accordance with some embodiments herein.

FIGS. 8A-8B are schematic illustrations of a use of an endoscope of the present disclosure to perform a medical imaging procedure on a vessel in accordance with some embodiments herein.

DETAILED DESCRIPTION

Figure 1:
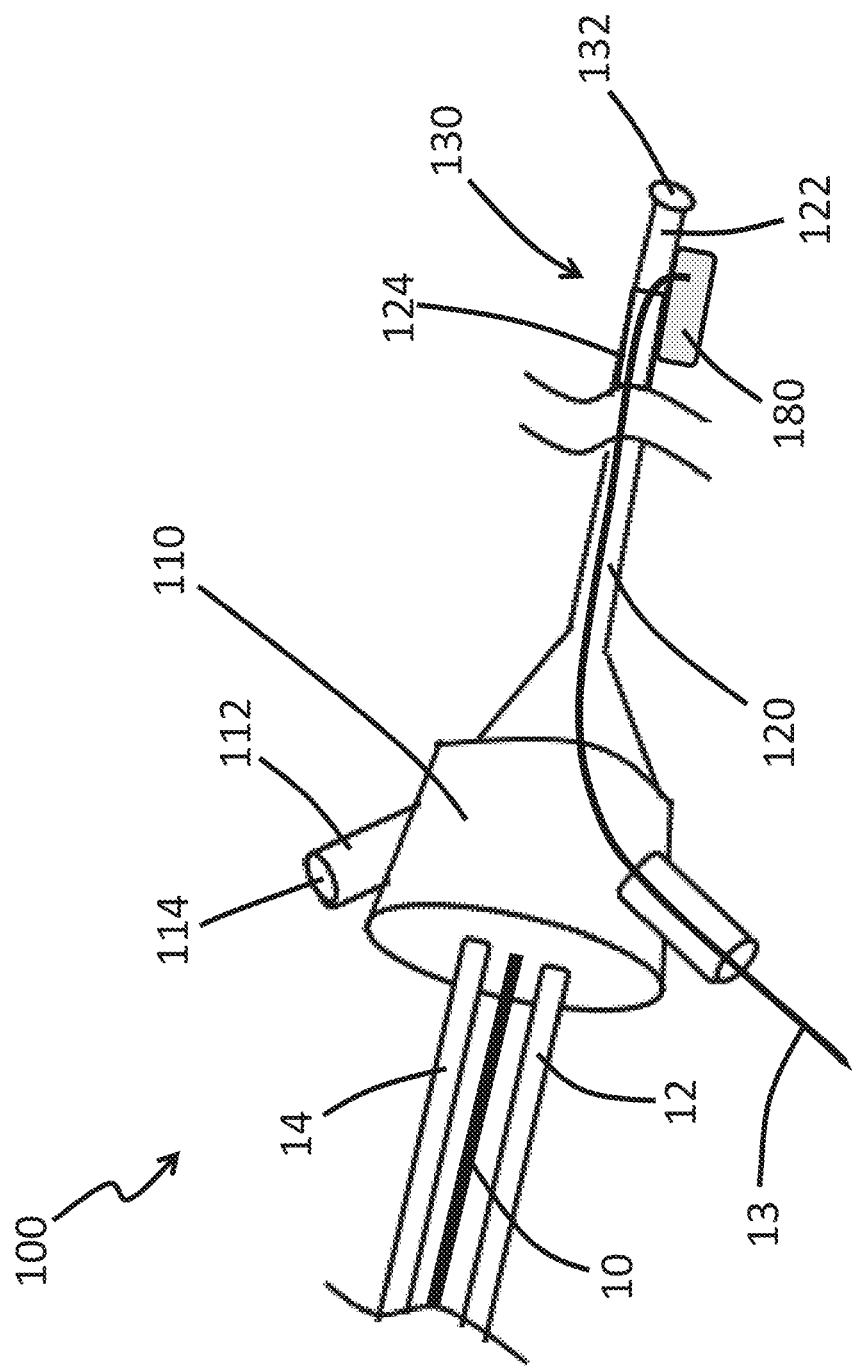
FIG. 1 is a schematic diagram of an endoscopy system in accordance with some embodiments herein.

Described herein are endoscopes (such as microendoscopes), endoscopy systems, and methods of using the same. Conventionally, visualization of the interior of vasculature has been indirect, for example via X-ray or ultrasound. The presence of fluid in vessels (such as blood in blood vessels) has conventionally limited direct imaging of the interior of vasculature, and thus can also limit the availability of surgical procedures that can be performed in the vessel. Described in some embodiments herein are endoscopes and endoscopy systems useful for direct imaging of the inside of a vessel (such as a blood vessel), and/or performing surgical procedures in the vessel and/or procedures that involve passing the endoscope through the vessel. In some embodiments, endoscopes and/or methods of using endoscopes are described. In some embodiments, the endoscope comprises a shaft having an image sensor within a distal tip of the shaft. The shaft can have an expandable cuff disposed on an outer surface of the shaft. The expandable cuff can be moved from a contracted configuration to a deployed configuration. With the expandable cuff in the deployed configuration, the expandable cuff and shaft can occupy all or substantially all of an interior area of a cross section of the vessel, thus inhibiting or preventing the flow of fluid (e.g., blood) in the vessel. Inhibiting, reducing, or preventing the flow of fluid (e.g., blood) can reduce or eliminate fluid downstream (relative to the fluid flow) of the expandable cuff, thus permitting direct visualization of the interior of the vessel by the image sensor without interference from the fluid. After the imaging or other medical procedure is complete, the expandable cuff can be moved back to the contracted configuration.

Endoscopes and Endoscopy Systems

In methods and endoscopes and systems of some embodiments, the endoscope comprises a shaft and an expandable cuff disposed around at least a portion of the shaft. An outer surface of the expandable cuff can be disposed further away from a longitudinal axis of the shaft when the expandable cuff is in a deployed configuration than when the expandable cuff is in a contracted configuration. The expandable cuff can be deployed while the endoscope is inside of a vessel (such as a blood vessel). The shaft and deployed expandable cuff can occupy all or substantially all of an interior area of a cross section of the vessel. It is contemplated that the microendoscope with the expandable cuff in the deployed configuration can thus inhibit, reduce, or stop fluidic flow (such as blood flow) inside the vessel, thus permitting visualization of the interior of the vessel and/or surgical procedures in the vessel. As used herein, an endoscope or portion thereof (e.g., a shaft portion and deployed expandable cuff) occupying "substantially all" of an interior area of a cross section of the vessel refers to occupying an interior area of the cross section of the vessel effective to inhibit, reduce, or prevent fluidic flow (such as blood flow) through the cross section, so as to permit visual imaging of the interior of the vessel without interference from fluid downstream (relative to fluid flow) of the occupied interior area of the vessel. It is noted that all or substantially all of the interior of the cross section of the vessel can be occupied in one, or more than one cross sections along the longitudinal axis of the vessel so as to reduce, inhibit, or prevent the flow of fluid. In some embodiments, substantially all of an interior area of a cross section of a vessel is occupied when at least 80%, 85%, 90%, 91%, 92%, 93%, 94%, 95%, 96%, 97%, 98%, 99%, 99.5%, 99.9%, or 100% of the interior area of the cross section of a vessel is occupied. While the term "expandable cuff" is used herein for conciseness, the expandable cuff may also be referred to herein as a "radially expandable cuff." As the expandable cuff as described herein may exert a radially-outward force on the interior of a vessel, the expandable cuff may also be referred to as an "expandable anchor." However, it will be appreciated in view of this disclosure that the expandable cuff or expandable anchor may reduce, inhibit or prevent the flow of fluid (such as blood) without necessarily remaining fixed axially along the length of a vessel. Accordingly, it will be appreciated that unless explicitly specified, the expandable cuff or expandable anchor as described herein is not necessarily stationary on a longitudinal axis of the vessel, even if the expandable cuff or expandable anchor is in a deployed configuration. In some embodiments, the deployed expandable cuff exerts a radially-outward force on an inside surface of a vessel. In some embodiments, the deployed expandable cuff helps to immobilize the endoscope inside the vessel during imaging and/or the procedure. In some embodiments, the endoscope comprises an expandable distal tip as described herein, which can permit the endoscope to have a sufficiently small diameter to advance through, image, and/or perform a surgical procedure in even small vessels, such as vasculature in the extremities or the brain. As used herein, unless stated otherwise, a "vessel" refers to a body vessel, for example a blood vessel or chamber of the heart. In some embodiments, an endoscope or endoscopy system as described herein is for medical use.

The endoscope or endoscopy system in accordance with some embodiments can include an endoscope comprising, consisting essentially of, or consisting of a hub, a shaft extending from the hub and comprising a distal tip and one or more expandable cuffs (such as a radially-expandable sleeves or protrusions) that are movable between a contracted configuration and a deployed configuration. It is noted that placing the expandable cuff in the deployed configuration may also be referred to herein as "deploying" the expandable cuff, or "expanding" the expandable cuff. An outer surface of the expandable cuff can be disposed further away from a longitudinal axis of the shaft when the expandable cuff is in the deployed configuration than when the expandable cuff is in the contracted configuration. As discussed herein, the expandable cuff in the deployed configuration and shaft can occupy all or substantially all of an interior area of a cross section of the vessel (such as a blood vessel or heart chamber), for example least 80%, 85%, 90%, 91%, 92%, 93%, 94%, 95%, 96%, 97%, 98%, 99%, 99.5%, 99.9%, or 100% of the interior area of the cross section of the vessel. It is contemplated that the deployed expandable cuff can thus inhibit, reduce, or prevent fluidic flow (such as blood flow) inside the vessel, thus permitting visualization of the interior of the vessel. In accordance with methods, endoscopes, and systems of some embodiments herein, the expandable cuff in the contracted configuration permits the movement of the endoscope shaft along a longitudinal axis of the vessel. In some embodiments, the endoscope further comprises an illuminating element within the distal tip. The illuminating element can be disposed to illuminate the field of view of the image sensor. In some embodiments, the endoscope further comprises an image sensor and an illuminating element disposed within the distal tip. Accordingly, when the expandable cuff is deployed, the microendoscope (and the expandable cuff and shaft in particular) inhibits, reduces, or prevents fluidic flow in the vessel (such as blood flow), thus permitting direct imaging of the interior of the vessel with the image sensor. For example, the expandable cuff and endoscope inhibiting, reducing, or preventing fluidic flow though the vessel can inhibit, reduce, or eliminate fluid downstream (relative to fluid flow) of the expandable cuff, so that the interior of the vessel can be directly imaged by the image sensor at the distal tip of the endoscope without interference from the fluid. In some embodiments, when deployed, the expandable cuff exerts a radial force against the interior of the vessel (such as blood vessel). In some embodiments, the radial force holds the endoscope in place. It is contemplated that holding the endoscope in place can facilitate local imaging. In some embodiments, the expandable cuff, when deployed, immobilizes or stabilizes the endoscope relative to surrounding tissue which can further facilitate imaging by the endoscope while it is immobilized. In some embodiments, the expandable cuff may hold the distal end of the endoscopy system fixed in the longitudinal direction relative to the vessel that surrounds the distal end such that the distal end does not move axially along the vessel when the expandable cuff is in the deployed configuration. In some embodiments, however, the expandable cuff in the deployed configuration may allow the distal end of the endoscope to move along the axial direction of the vessel that surrounds the distal end. In some embodiments, the expandable cuff is adapted to stabilize or immobilize the distal tip of endoscope relative to the surrounding tissue when the expandable cuff is in the deployed configuration. For example, in some embodiments the expandable cuff can be moved into the deployed configuration to move the outer surface of the expandable cuff against a lumenal surface (which may also be referred to as an "inner" or "inside" surface) of a blood vessel or heart chamber that surrounds the endoscopy system. In some embodiments, when deployed, the expandable cuff has a diameter that is within about 20% of the diameter of the vessel or heart chamber, for example within 20%, 15%, 10%, 5%, 4%, 3%, 2%, or 1% of the diameter of the blood vessel or heart chamber. The expandable cuff can be deployed to exert a radially-outward force on an inside surface of a vessel (such as a blood vessel or heart chamber) through which the endoscopy system is advanced. The expandable cuff can include features to inhibit, mitigate, or avoid damage to the surrounding tissue upon which the expandable cuff is deployed. The endoscope can be arranged to inhibit, mitigate, or avoid damage to the surrounding tissue when the expandable cuff is deployed. The endoscope can further comprise an image sensor within the distal tip.

In some embodiments, endoscopy systems are described. The endoscopy system can comprise, consist essentially of, or consist of an endoscope as described herein. It is understood herein that when the term "endoscope" or "microendoscope" is mentioned herein (including variations of this root term), an endoscopy system comprising, consisting essentially of, or consisting of the endoscope is also expressly contemplated. Additionally, it is understood that when "endoscopy systems" (including variation of this root term) are mentioned herein, endoscopy systems comprising, consisting of, or consisting essentially of an endoscope such as a microendoscope are expressly contemplated. Endoscopy systems comprising, consisting essentially of, or consisting of only a single endoscope are expressly contemplated, but unless expressly stated, endoscopy systems are described herein are not necessarily limited to only a single endoscope. In some embodiments, the endoscopy system further comprises a guidewire. In some embodiments, the endoscopy system further comprises an illumination source, such as a laser. The illumination source can be in optical communication with the illumination element as described herein, or can be adapted to be placed in optical communication with the illumination element as described herein. In some embodiments, the endoscopy system further comprises an inflation pump. The inflation pump can be in fluid communication, or can be adapted to be place in fluid communication with an internal space of the expandable cuff It will be appreciated in view of this disclosure that in view of the size of the vessel of interest, a suitable scale of endoscope and expandable cuff can be selected such that the deployed expandable cuff and shaft can occupy all or substantially all of an interior area of a cross section of the blood vessel. Thus, in the case of larger vessels (such as pulmonary veins, which can have inner diameters greater than 1 cm), a larger diameter of endoscope shaft and deployed expandable cuff may be suitable for the endoscope to occupy all or substantially all of an interior area of a cross section of the vessel. As such, an "endoscope" as described herein is not necessarily limited to endoscopes less than 1 cm in diameter. Rather, suitable endoscopes and expandable cuff and shaft scales sufficient to occupy all or substantially all of an interior area of a cross section of the vessel are contemplated in accordance with endoscopes (such as microendoscopes), endoscopy systems, and methods herein. In some embodiments, the endoscope exerts a radially-outward force on the vessel.

The endoscope can include a working channel that is sized to allow a tool to be inserted into the working channel. The working channel can be configured to allow a tool inserted into the working channel to be advanced along the working channel to reach a distal end of the endoscope. In some embodiments, the working channel can have an opening at a distal end of the working channel, thereby allowing a distal portion of the tool to exit the distal end of the endoscope. A distal portion of the working channel can be distensible and a longitudinally overlapping portion of an outer sheath of the shaft can also be deformable, allowing the profile of the endoscope to expand as a tool within the working channel moves distally past an element (e.g., image sensor) within the lumen of the endoscope. It is also contemplated that in some embodiments, the endoscope comprises a tool, but without a working channel. By way of example, the tool can be advanced longitudinally along the shaft and past the image sensor to the distal end of the endoscope without passing through a working channel.

In endoscopes, systems, and method of some embodiments, the expandable cuff includes a pliable portion and a reinforced portion. The pliable portion can be more distensible than the reinforced section. The expandable cuff can be adapted so that the reinforced section contacts and presses against a surrounding tissue when the expandable cuff is deployed. In some arrangements, the pliable portion can be arranged so that it does not contact the surrounding tissue when the expandable cuff is deployed. In some embodiments, the pliable portion can further distend to accommodate increased contact pressure between the reinforced portion and the surrounding tissue such that the contact area between the reinforced portion and the surrounding tissue is stabilized, for example to avoid or inhibit puncturing, tearing, or abrasion of the surrounding tissue. In some embodiments, the pliable portion distends to accommodate increased contact pressure thereby maintaining a stable contact area of the reinforced portion with the inner surface of the vessel and mitigating or avoiding the reinforced portion from pressing against and damaging additional areas of the endothelium of the vessel. As such, it is contemplated that the contact area of the reinforced portion with the inner surface of the vessel wall can remain relatively unchanged in response to pressure fluctuations on the expandable cuff, and thus can avoid or mitigate damage to the endothelium of the vessel. Stabilizing the contact area between the expandable cuff and the surrounding tissue can reduce or avoid damage to the surrounding tissue when the expandable cuff is deployed (to immobilize or stabilize the endoscopes relative to the surrounding tissue). It is noted that in contrast to systems such as balloon angioplasty systems, which can be configured for movement of an inflated balloon in a vessel, expandable cuffs of endoscopes of some embodiments herein are configured to immobilize and/or stabilize the shaft of an endoscope at a position within a vessel. However, as disclosed herein, in some embodiments, the endoscopes and endoscopy systems can include features configured for one or more medical procedures such as angioplasty, electrocauterization, cryotherapy, neuroablation, clot removal, device implantation. Accordingly, in some embodiments, the endoscope is not configured for angioplasty. In some embodiments, the expandable cuff does not comprise, consist essentially of, or consist of an angioplasty balloon. Rather than be moved through a vessel, the expandable cuff of some embodiments can be configured to immobilize the endoscope in the vessel. For example, the expandable cuff can be arranged to stabilize or immobilize the illuminating element and image sensor while imaging is performed within a vessel, and/or as a tool moves through the working channel and longitudinally past the image sensor. Furthermore, it is contemplated that expandable cuffs of endoscopes of some embodiments herein, by stabilizing vascular tissue when in the deployed state, can have minimal impact on this tissue, and thus are configured to have a minimal or no physiological impact on the tissue once they have finished being deployed. Thus, in some embodiments, following deployment and subsequent removal from a blood vessel or heart chamber, the expandable cuff does not induce any appreciable physiological change to the vessel or heart chamber. In some embodiments, the endoscopy system is configured for percutaneous access to the vessel.

FIG. 1 depicts a generalized endoscope 100 in accordance with some embodiments. The endoscope 100 can include a hub 110, which remains outside the patient's body. The hub 110 can be used by the operator to manipulate the endoscope 100, as described more fully below. An elongated, flexible shaft 120 can extend from that hub 110. The shaft 120 can be inserted into the patient's body. The shaft 120 can connect the hub 110 to a distal tip 130 of the endoscope 100. The shaft 120 can have an opening 132 at the distal tip 130 of the endoscope 100. The shaft 120 can be hollow or include one or more lumens. The opening 132 can provide a path for the interior space of the shaft 120 (or the interior space of a lumen within the shaft) to communicate with the outside environment. For example, the opening 132 can allow the interior space of the shaft 120 to communicate with an internal cavity of a patient when the shaft 120 is inserted through an incision in the skin of the patient. The opening 132 can allow the interior space of the shaft 120 to communicate with an internal space of a vessel (e.g., blood vessel) or a heart chamber of a patient when the shaft 120 is inserted endovascularly in the patient, for example for direct imaging of the interior of the vessel or heart chamber with an image sensor in the distal tip as described herein (See, e.g., the distal tip 130 and image sensor 140 of FIG. 2).

The hub 110 can include one or more ports 112. As described in more detail below, an item (e.g., tool, flushing fluid) can be inserted into a proximal opening 114 of the port 112, advanced along the interior of the shaft 120, and passed through the opening 132 at the distal end 130 of the shaft 120. The hub 110 can be adapted to receive a guidewire 10. For example, in the illustrated embodiment, the endoscope 100 is mounted onto a guidewire 10 in an over-the-wire configuration. The endoscope 100 can be mounted onto a guidewire 10 in a rapid exchange configuration. In some embodiments, the endoscope 100 in the contracted state is configured to ride along a guidewire 10 through a blood vessel. In some embodiments, the endoscope 100 can include a guidewire lumen that is sized to receive a guidewire 10, as shown in FIG. 1. In some embodiments, the endoscope 100 can be configured to enter the deployed configuration while the guidewire 10 is disposed in the guidewire lumen. As shown in FIG. 1, a proximal end of the guidewire lumen can be disposed on the hub 110. The endoscope 100 can include data communication lines 12 and/or power lines 14. The hub 110 can be configured to allow data communication lines 12 and/or power lines 14 to extend out of the hub 110. The data communication line 12 can transmit data (e.g., image sensor data) to an electronic device (e.g., display screen). The power line 14 can provide power to electronics housed within the hub 112 or at another location of the endoscope 100.

The shaft 120 can include an expandable cuff 180 such as an radially-expandable sleeve as described herein. The expandable cuff 180 can be movable between a contracted configuration and a deployed configuration. A distance of an outer periphery of the expandable cuff 180 from a longitudinal axis of the shaft 120 can be greater when the expandable cuff 180 is in the deployed configuration compared to when the expandable cuff 180 is in the contracted configuration. The expandable cuff 180 can be moved from the contracted configuration to the deployed configuration by inflating an internal space of the expandable cuff 180. For example, the endoscope 100 can have an inflation channel 13 that extends from the hub 110 to an internal space of the expandable cuff 180, as depicted in FIG. 1. A fluid (e.g., saline) and/or gas can be passed through the inflation channel 13 from the hub 110 to the internal space of the expandable cuff 180 to fill the internal space of the expandable cuff 180. The expandable cuff 180 can be moved from the contracted configuration to the deployed configuration by adding or pressurizing fluid within an internal space of the expandable cuff 180. The expandable cuff 180 can be moved from the deployed configuration to the contracted configuration by removing or depressurizing fluid within an internal space of the expandable cuff 180. When the expandable cuff is deployed, the endoscope can occupy all or substantially all of an interior area of a cross section of a specified vessel. In some embodiments, when the expandable cuff is deployed, the endoscope can thus inhibit, reduce, or stop fluidic flow (such as blood flow) inside the vessel, thus permitting visualization of the interior of the vessel and/or surgical procedures in the vessel In the illustrated embodiment, the endoscope 100 has one flow channel 13 that is fluidically connected to one expandable cuff 180. The flow channel 13 can be for inflation of the expandable cuff 180. As disclosed herein, the endoscope 100 can include one or more than one expandable cuffs 180 and one or more than one flow channels 13. The one or more expandable cuffs 180 can be fluidically connected to the one or more flow channels 13. A flow channel 13 can be fluidically connected to one or more than one expandable cuffs 180. An expandable cuff 180 can be fluidically connected to one or more than one flow channels 13.

The shaft 120 can include an expandable portion 122. The expandable portion 122 can be adapted to reversibly expand. The expandable portion 122 can be configured to expand radially to allow items that have a large profile to push distally past other components of the endoscope 100 that are located at the expandable portion 122 of the shaft 120. For example, the expandable portion 122 can surround a camera lens that occupies a large size profile. The expandable portion 122 can expand to allow tools to navigate distally past the camera lens.

The shaft 120 can include a rigid portion 124. The rigid portion 124 can be adapted so that it does not reversibly expand. The rigid portion 124 can be longitudinally aligned with portions of the shaft 120 that need not expand to allow a large profile item to advance distally toward the opening 132. For example, the rigid portion 124 can surround fiber optic fibers, electrical cords, or other low-profile items that do not require the shaft 120 to radially expand to allow a tool to advance past these low-profile items.

The expandable cuff 180 can be arranged to be entirely within the expandable portion 122. In some arrangements, the expandable cuff 180 can be disposed entirely within the rigid portion 124. In some embodiments, the expandable cuff 180 can be disposed on the shaft 120 (integrally or in a separate piece) such that a first portion of the expandable cuff 180 is disposed on the expandable portion 122 and a second portion of the expandable cuff 180 is disposed on the rigid portion 124, as shown in FIG. 1.

In some embodiments, the distal portion of the shaft 120 that is inserted into the patient can have an outer diameter of about 2 mm. In some embodiments, the outer diameter of the shaft is about: 0.5 mm, 0.6 mm, 0.8 mm, 1.0 mm, 1.5 mm, 2.0 mm, 3.0 mm, 4.0 mm, or 5.0 mm, including ranges between any two of the listed values. In some arrangements, the outer diameter of the shaft 120 is between the range of 0.5 mm to 5.0 mm, 1.0 mm to 4.0 mm, 2.0 mm to 3.0 mm, or 1.5 mm to 2.5 mm. In some embodiments, for example if a larger vessel is of interest, the outer of the diameter of the shaft is larger, for example, up to about 10 mm, 20 mm, 50 mm, 100 mm, 200 mm, 500 mm, 1000 mm, 1500 mm, or 2000 mm, including ranges between any two of the listed values, for example 10-2000 mm, 10-1000 mm, 10-500 mm, 100-2000 mm, 100-1000 mm, or 100-500 mm.

Figure 2B:
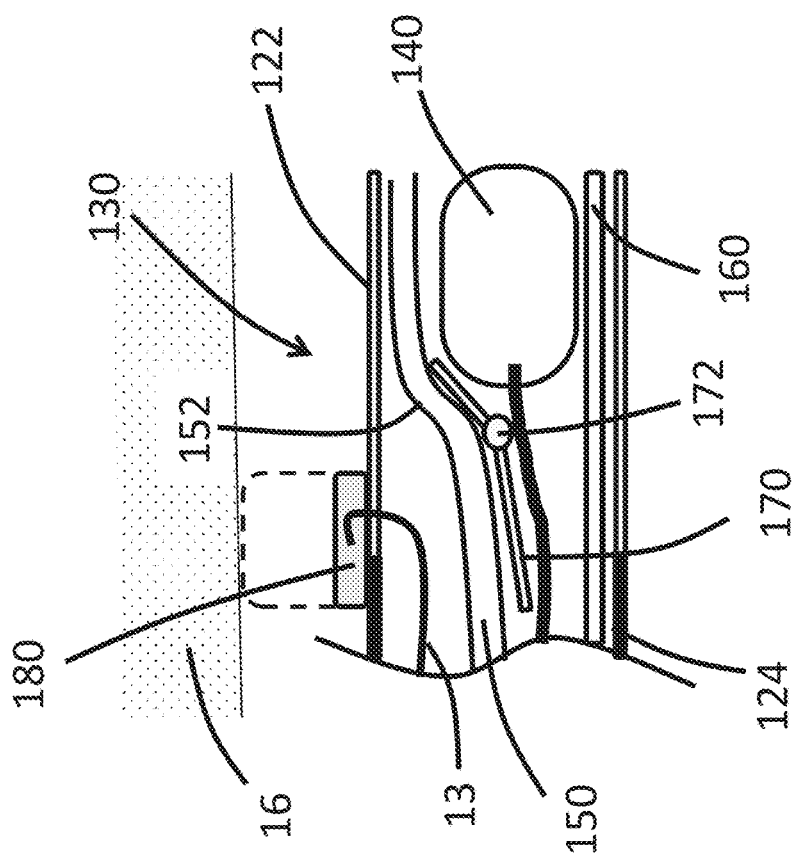
FIG. 2B is a cross-sectional side view of a distal tip of an endoscope comprising a working channel in accordance with some embodiments herein.
Figure 2A:
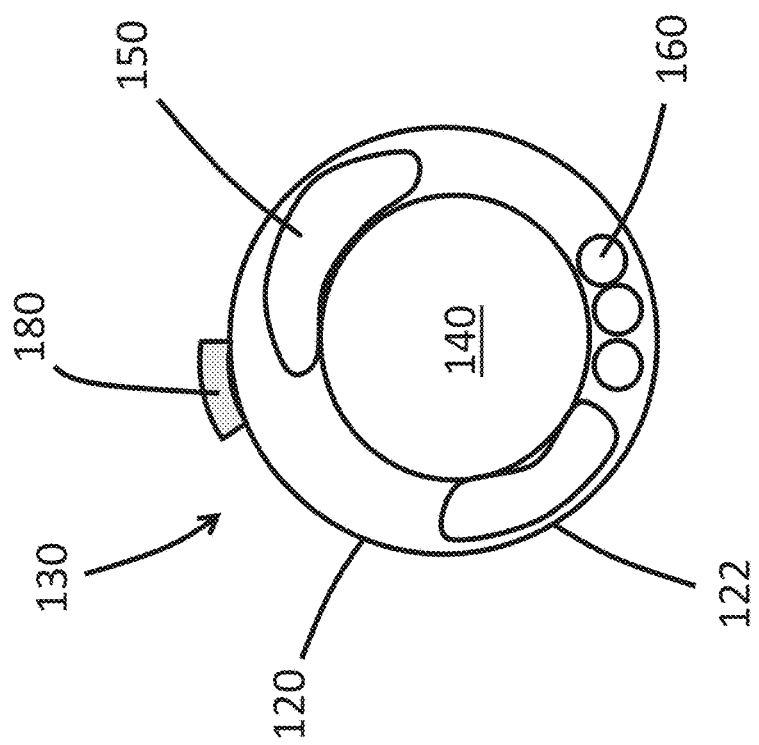
FIG. 2A is an end view of a distal tip of an endoscope comprising a working channel in accordance with some embodiments herein.

FIG. 2A shows an end view of a non-limiting, illustrative embodiment of a distal tip 130 of the endoscope 100. The expandable portion 122 of the shaft 120 can surround an image sensor 140. The expandable cuff 180 can be disposed on an outer surface of the shaft 120. One more working channels 150 can be disposed within the lumen of the shaft 120. The working channels 150 can be sized to allow an item such as a tool to be passed through the working channel 150 to reach the distal tip 130 of the endoscope 100. In the illustrated embodiment, the distal tip 130 includes two working channels 150 that are disposed radially outward of the image sensor 140. In some embodiments, the distal tip 130 includes only one working channel 150. In some arrangements, the endoscope 100 includes three or more working channels 150. As discussed below, the working channel 150 can include a distensible portion that can reversibly deform to allow the cross-sectional area of the lumen of the working channel 150 to increase. The working channel 150 can allow one or more tools to be deployed from the endoscope 100 to perform a medical procedure such as imaging, biopsy, angioplasty, electrocauterization, cryotherapy, neuroablation, clot removal, aneurism reinforcement, device implantation. As discussed, the endoscope 100 can include a guidewire lumen. In some embodiments, the working channel 150 includes the guidewire lumen. In some embodiments, the guidewire lumen is a lumen that is separate and distinct (e.g., spaced apart) from the working channel 150.

With continued reference to FIG. 2A, the distal tip 130 can include illumination fibers 160. In the illustrated embodiment, the distal tip 130 includes three illumination fibers 160. In some embodiments, the distal tip 130 includes only one illumination fiber 160. In some arrangements, the endoscope 100 includes two, three, or more than three illumination fibers 160. Optionally the illumination fibers 160 can be in optical communication with a laser light source. In at least one embodiment, the endoscope 100 can include only one illumination fiber 160 and that single illumination fiber 160 is coupled to a laser light source, thereby allowing the single illumination fiber 160 to provide enough light to adequate illuminate the tissue space for imaging with the image sensor 140.

FIG. 2B shows a cross-sectional side view of another embodiment of a distal tip 130. The expandable cuff 180 can be fluidically connected to an inflation channel 13. The expandable cuff 180 can move from a contracted configuration (illustrated in FIG. 2B as solid line) to a deployed configuration (illustrated in FIG. 2B as dashed line). When the expandable cuff 180 is in the deployed configuration, the endoscope 100 can occupy all or substantially all of an interior area of a cross section of a surrounding tissue such as a vessel 16. In some embodiments, when the expandable cuff 180 is in the deployed configuration, fluidic flow (e.g., blood flow) in the vessel 16 is inhibited, reduced, or prevented, thus permitting visualization of the interior of the vessel and/or surgical procedures in the vessel. In some embodiments, when the expandable cuff 180 is deployed, the microendoscope occupies at least 80%, 85%, 90%, 91%, 92%, 93%, 94%, 95%, 96%, 97%, 98%, 99%, 99.5%, 99.9%, or 100% of the interior area of the cross section of the vessel. In some embodiments, the expandable cuff 180 compresses the surrounding tissue 16 when the expandable cuff 180 is in the deployed configuration. The expandable cuff 180 can stabilize or immobilize at least a portion of the endoscope 100 relative to the surrounding tissue 16 when the expandable cuff 180 is in the deployed configuration. In some arrangements, the expandable cuff 180 is adapted to stabilize or immobilize the distal tip 130 relative to the surrounding tissue 16 when the expandable cuff 180 is in the deployed configuration. In some embodiments, the expandable cuff 180 is adapted to hold the distal tip 130 fixed in the longitudinal direction relative to the surrounding tissue when the expandable cuff 180 is in the deployed (e.g., radially-expanded) configuration. In some embodiments, the expandable cuff 180 allows the distal tip 130 to move in the axial direction of the surrounding vessel when the expandable cuff 180 is in the deployed (e.g., radially-expanded) configuration.

The expandable cuff 180 can have an outer diameter in the deployed configuration that is slightly larger than an internal diameter of a surrounding blood vessel such that the expandable cuff 180 can exert a radially-outward force on the inside surface of the surrounding blood vessel. The expandable cuff 180 can be sized to exert a radially-outward force on a vessel selected from the group consisting of a pulmonary artery, a pulmonary vein, a peripheral artery, a peripheral vein, a radial artery, an inferior vena cava, a superior vena cava, an iliac vein, an iliac artery, a femoral vein, a femoral artery, an aorta, a carotid artery, a coronary artery, or two or more of the listed vessels. The expandable cuff 180 can be sized so that in the deployed configuration the outer surface of the expandable cuff 180 is disposed away from a longitudinal axis of the endoscope 100 by a deployed radius. The endoscope 100 can have a deployed radius of: 0.5 mm, 1.0 mm, 1.5 mm, 2.0 mm, 3.0 mm, 5.0 mm, 10 mm, and other values between the listed values. In some embodiments, the endoscope 100 has a deployed radius that is within ±20%, ±15%, ±10%, ±5%, ±4%, ±3%, ±2%, or ±11% of the radius of a specified vessel or section thereof in which the endoscope is to be immobilized. In some embodiments, the endoscope 100 has a deployed radius that is configured to inhibit, reduce, or stop fluid flow (such as blood flow) in the specified vessel (such as a blood vessel).

The distal tip 130 can include a ramp 170 that is adapted to guide the working channel 150 around the image sensor 140. The ramp 170 can be arranged so that an item (e.g., tool) that is advanced within the working channel 150 past the image sensor 140 does not impact or alter the orientation of the image sensor 140. The ramp 170 can protect the image sensor 140 from being knocked out of proper alignment when an item within the working channel 150 advances past the image sensor 140. In the illustrated embodiment, the distal tip 130 has only one working channel 150. However, the endoscope 100 can include additional working channels 150 and ramps 170 that protect the sensor 140 from being knocked out of alignment. In some configurations, the ramp 170 can be anchored to the rigid portion 124 of the shaft 120. For example, the ramp 170 can include a pin 172 that is connected to the rigid portion 124 by a strut (not shown).

As discussed, the working channel 150 can include a distensible portion 152 that longitudinally aligns with the expandable portion 122 of the shaft 120. As an item (e.g., tool) is advanced distally along the working channel 150, the ramp 170 directs the item away from the image sensor 140, thereby protecting the alignment of the image sensor 140. As the item passes by the image sensor 140, the distensible portion 152 of the working channel 150 radially expands to allow the item to pass by the image sensor 140 without disrupting the position of the image sensor 140. The radial expansion of the distensible portion 152 of the working channel 150 can cause the expandable portion 122 of the shaft 120 to radially expand to accommodate the profile of the item passing by the image sensor 140. Once the item in the working channel 150 is no longer longitudinally aligned with the image sensor 140, the distensible portion 152 and the expandable portion 122 can deform back to a low-profile configuration.

As shown in FIG. 2B, the expandable cuff 180 can longitudinally overlap with at least a portion of the expandable portion 122. In some arrangements, the expandable cuff 180 can longitudinally overlap with at least a portion of the distensible portion 152 of the working channel 150. As discussed herein, when the expandable cuff 180 is in the deployed position, all or substantially all of an interior area of a cross section of the surrounding tissue such as a vessel 16 can be occupied, thus inhibiting, reducing, or preventing fluidic flow (such as blood flow) inside the vessel 16. In some embodiments, the expandable cuff 180 can be arranged to maintain positioning of the endoscope 100 with respect to the surrounding tissue such as a vessel 16 as an item (e.g. tool) passes by the image sensor 140 to exit the distal tip 130. The expandable cuff 180 can minimize or reduce damage to the surrounding tissue such as the vessel 16 as the item passes by the image sensor 140 to exit the distal tip 130. In some arrangements, the expandable cuff 180 can be arranged to maintain positioning of the endoscope 100 with respect to the surrounding tissue such as a vessel 16 while the image sensor 140 performs local imaging.

Additional information about endoscopes, including endoscopes and features of endoscopes suitable in accordance with some embodiments herein, can be found in PCT Pub. No. WO 2017/027299 and US Pub. No. 2017/0035277, each of which is hereby incorporated by reference in its entirety. In endoscopes, systems, and methods of some embodiments, the endoscope comprises, consists essentially of, or consists of an endoscope or microendoscope as described in PCT Pub. No. WO 2017/027299 and/or US Pub. No. 2017/0035277. The endoscope can further comprise an expandable cuff as described herein.

FIGS. 3A-3D illustrate side views of different arrangements in which the expandable cuff 180 can be used with the endoscope 100. As discussed herein, the endoscope 100 can include only one expandable cuff 180 or can include more than one expandable cuff 180. The more than one expandable cuff 180 can be similar to one another in the deployed configuration, in the contracted configuration, or in both the deployed configuration and the contracted configuration.

As shown in FIG. 3A, the expandable cuff 180 can comprise two spaced-apart expandable cuffs 180 that are disposed entirely within the rigid portion 124 and circumferentially surround a longitudinal axis 5 of the endoscope 100 of some embodiments. As shown in FIG. 3A, each of the two expandable cuffs 180 can be similar in shape to one another in the deployed configuration. As shown in FIG. 3B, the expandable cuffs 180 can be disposed entirely upon (integrally or in a separate piece from) the expandable portion 122 of the endoscope 100. As shown in FIG. 3C, the endoscope 100 can include an expandable cuff 180 that is disposed entirely upon (integrally or in a separate piece from) the rigid portion 124 (or the expandable portion 122) and an expandable cuff 180 that spans portions of both the expandable portion 122 and the rigid portion 122. FIG. 3D, shows the endoscope 100 can include a first expandable cuff 180a that has a greater radial expansion in the deployed configuration compared to a second expandable cuff 180b. The endoscope 100 can include expandable cuffs 180 that are combinations of the different embodiments shown in FIGS. 3A-3D.

FIGS. 4A-4E illustrate end views of the shaft 120 illustrating arrangements of the expandable cuff 180 that can be used with the endoscope 100 of some embodiments. As shown in FIG. 4A, the expandable cuff 180 can entirely circumferentially surround a longitudinal axis 5 of the endoscope 100. In some embodiments, the expandable cuff 180 can only partially circumferentially surround the longitudinal axis 5. As shown in FIG. 4B, the endoscope 100 can include a pair of the expandable cuffs 180 that are circumferentially disposed around the shaft 120 and are similar in shape to one another. FIG. 4C illustrates the endoscope 100 can have circumferentially expandable cuffs 180 that are different in shape compared to one another. The expandable cuffs 180 can differ in shape relative to one another with regard to the extent the expandable cuff 180 circumferentially surrounds the longitudinal axis. The expandable cuffs 180 can differ in shape relative to one another with regard to the extent the expandable cuffs 180 extend away from the longitudinal axis 5. The expandable cuffs 180 can differ in shape to one another in the deployed configuration, in the contracted configuration, or both the deployed configuration and the contracted configuration. FIG. 4D illustrates that the endoscope 100 can include more than one expandable cuffs 180 that are equally distributed circumferentially about the shaft 120. FIG. 4E illustrates that the endoscope 100 can include expandable cuffs 180 having combinations of the features disclosed herein. In some embodiments, the expandable cuffs 180 are circumferentially disposed and around the shaft 120, and are equally distributed. In some embodiments, the expandable cuffs 180 are circumferentially disposed around the shaft 120, and unequally distributed around the shaft 120.

FIG. 5 illustrates a partial side view of a distal tip 130 having a tool 300 that extends distally beyond the image sensor 140 of the endoscope 100. In some embodiments, the tool 300 is adapted to deploy a heart valve. In some embodiments, the tool 300 is adapted to perform an ablation procedure. In some embodiments, the tool 300 is adapted to perform an arthroplasty procedure. In the illustrated embodiment, the endoscope 100 has only one expandable cuff 180 and that expandable cuff 180 longitudinally overlaps with a portion of the expandable portion 122 and the rigid portion 124 of the shaft 120. The expandable cuff 180 can be arranged in a configuration different from that shown in FIG. 5 or may be accompanied with one or more additional expandable cuffs 180, as discussed herein.

Figure 6:
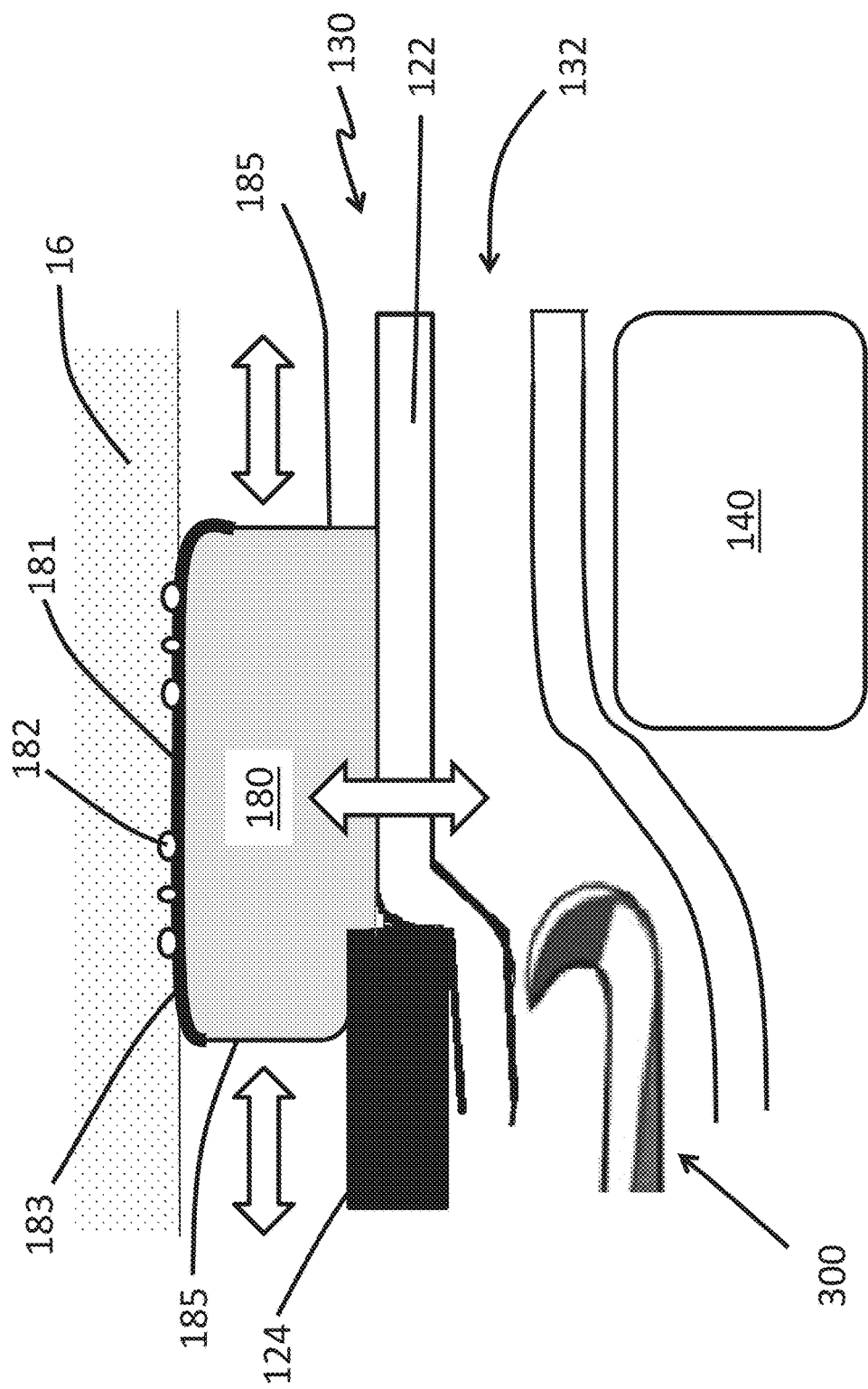
FIG. 6 is a partial side view of a distal tip of an endoscope comprising an expandable cuff in accordance with some embodiments herein.

FIG. 6 illustrates a partial side view of the distal tip 130 with a tool 300 being advanced distally within the working channel 150 toward the opening 132. In the illustrated embodiment, the endoscope 100 includes an expandable cuff 180 that longitudinally overlaps a portion of the expandable portion 122. The expandable cuff 180 is shown in the deployed configuration. An outer surface 181 of the expandable cuff 180 is in contact with the surrounding tissue 16. The expandable cuff 180 can include a surface texture 182 such as pebbling, knurling, or other similar surface textures to enhance the interaction between the expandable cuff 180 and the surrounding tissue 16. The surface texture 182 can be adapted to increase the frictional forces between the expandable cuff 180 and the surrounding tissue 16. The surface texture 182 can be adapted to promote an atraumatic interaction between the expandable cuff 180 and the surrounding tissue 16 such that the damage to the surrounding tissue 16 is inhibited, mitigated, or minimized as the expandable cuff 180 presses against the surrounding tissue 16 to stabilize or immobilize the endoscope 100.

FIG. 6 shows that the expandable cuff 180 can include a reinforced portion 183 that is less distensible compared to a pliable portion 185. The reinforced portion 183 can formed by including, imbedding, or overlaying material in the reinforced portion 183. The included reinforcement material can be stiffer than the material of the pliable portion 185. The expandable cuff 180 can be arranged such that the compliance or distensibility of the reinforced portion 183 and the pliable portion 185 match one another until a threshold expansion ratio has been reached. An expansion ratio can be defined as the ratio between the outer dimension of the expandable cuff 180 in the deployed state compared to the outer dimension of the expandable cuff 180 in the contracted state. The expandable cuff 180 can be arranged such that the compliance or distensibility of the reinforced portion 183 is reduced compared to that of the pliable region 185 when the expansion ratio of the expandable cuff 180 exceeds the threshold expansion ratio.

As illustrated in FIG. 6, the expandable cuff 180 can be arranged so that as the tool 300 passes by the image sensor 140, the expandable portion 122 of the shaft expands radially outward and toward the surrounding tissue 16 (as indicated by the vertical double-headed open arrow). The expandable cuff 180 can be arranged so that as the expandable portion 122 moves away from the image sensor 140 and toward the surrounding tissue 16, the pliable portion 185 expands longitudinally (as indicated by the horizontal double-headed open arrow) to accommodate the inflation fluid (or gas) within the expandable cuff 180 that is displaced by the movement of the expandable portion 122 away from the image sensor 140 and toward the surrounding tissue 16. The expansion of the pliable region 185 in the longitudinal direction can allow the contact area between the expandable cuff 180 and the surrounding tissue 16 to remain substantially unchanged as the tool 300 moves distally past the image sensor 140.

While FIG. 6 illustrates an expandable cuff 180 that spans the interface of the expandable portion 122 and the rigid portion 124 of the shaft 120, the expandable cuff 180 can be disposed entirely upon (integrally or as a separate part) the rigid portion 124 or entirely within the expandable portion 122. The endoscope 100 can include an expandable cuff 180 that is disposed entirely upon (integrally or as a separate part) the rigid portion 124 and includes the reinforced and pliable portions 183, 185. The pliable portion 185 can distend to maintain a substantially unchanged footprint between the expandable cuff 180 and the surrounding tissue such as a vessel 16 as the compressive force between the expandable cuff 180 and the surrounding tissue such as a vessel 16 varies (such as due to a contraction of the surrounding tissue or applying a torque to the endoscope 100).

Also, FIG. 6 illustrates that expandable cuff 180 can include a pliable portion 185 that expands longitudinally along rigid portion 124 and longitudinally along the expandable portion 122. The expandable cuff 180 can include more than one pliable portion 185. The expandable cuff 180 can have a first pliable portion 185 that expands longitudinally along the rigid portion 124 and a second pliable portion 185 that expands longitudinally along the expandable portion 122.

Endoscopes Comprising Expandable Cuffs and Methods of Using

In some embodiments, the endoscope or endoscopy system comprises an expandable cuff such as a radially-expandable protrusion or sleeve as described herein. In some embodiments, the expandable cuff in the deployed condition and shaft (and thus the endoscope) occupy all or substantially all of an interior area of a cross section of the vessel, so as to inhibit, reduce, or prevent fluidic flow (such as blood flow) inside the vessel. For example, at least 80%, 85%, 90%, 91%, 92%, 93%, 94%, 95%, 96%, 97%, 98%, 99%, 99.5%, 99.9%, or 100% of the interior area of the cross section of a vessel can be occupied. Thus, the interior of the vessel downstream (relative to the fluid flow) of the expandable cuff can be directly imaged without interference from fluid. In some embodiments, the expandable cuff is deployed by introducing fluid or gas into an internal space of the expandable cuff. In some embodiments, the expandable cuff can be deployed by other methods such as heating or unsheathing a shape memory material. In some embodiments, the expandable cuff is adapted to immobilize or stabilize a portion of the endoscope as a medical procedure is performed on a tissue of a patient by tools extending through the endoscope and distally past the opening of the distal tip. The expandable cuff can be sized to brace the endoscope against an inside surface of a blood vessel or heart chamber.

In some embodiments, a method of imaging an interior of a vessel includes advancing an endoscope as described herein within a vessel to a target location. The method can further include expanding the expandable cuff of the endoscope to the deployed configuration, so the expandable cuff and shaft occupy all or substantially all of an interior area of a cross section of the vessel. The microendoscope with the expandable cuff in the deployed configuration can thus inhibit, reduce, or prevent fluidic flow (such as blood flow) inside the vessel, thus permitting visualization of the interior of the vessel and/or surgical procedures in the vessel (e.g., without interference from the fluid). The method further comprises imaging a field of view in the interior of the vessel while the fluid (e.g., blood) flow is inhibited, reduced, or prevented. The method can further comprise contracting the expandable cuff. In some embodiments, the method further comprises resuming moving the expandable endoscope toward the target location along the guidewire after the field of view has been imaged. In some embodiments, when the expandable cuff is deployed, an outer surface of the expandable cuff contacts two or more portions of an inner surface of the vessel, in which the portions are circumferentially disposed around the endoscope. In some embodiments, advancing the endoscope includes moving the endoscope along a guidewire toward the target location. In some embodiments, the method further includes halting the endoscope along the guidewire, expanding the expandable cuff such that the expanded expandable cuff inhibits, reduces, or prevents fluid (e.g., blood) flow in the vessel. In some embodiments, the vessel in which the method is performed is a blood vessel, for example a radial artery or a femoral artery. In some embodiments, the method is performed in a coronary artery and the target location includes a portion of the coronary artery that includes an obstruction. In some embodiments, the vessel in which the method is performed is a chamber of the heart. Wherever a method of imaging comprising an endoscope is described herein, also contemplated is an endoscope for use in imaging.

In some embodiments, the endoscope is loaded onto a guidewire after the guidewire has been placed in the patient. For example, a guidewire can be advanced endovascularly until a distal end of the guidewire is at or near the target location (by way of example, the guidewire can be positioned using fluoroscopy). The distal end of the guidewire can remain in place at or near the target location while a proximal end of the guidewire is fed through the distal end of the endoscope and advanced proximally through the endoscope until the proximal end of the guidewire emerges from a proximal end of the endoscope. The endoscope can then be advanced along the guidewire to bring the distal end of the endoscope to the target location. In this way, the relative movement between the guidewire and the endoscope is directed toward the proximal end of the endoscope. This can avoid kinking the guidewire or damaging portions of the endoscope, which could result if the guidewire were fed distally through the endoscope from the proximal end of the endoscope. In some embodiments of the method, the guidewire can be fed through the distal end of the endoscope before introducing the guidewire into a vessel of the patient. In other words, the endoscope can be loaded onto the guidewire first and then the guidewire can be placed within the patient while the endoscope is loaded onto the guidewire.

EXAMPLES

Example 1

An endoscopy system for performing a heart-valve-repair procedure includes a shaft comprising a deformable outer sheath that circumferentially surrounds an image sensor, an illuminating element. An expandable cuff is coupled to the shaft of the endoscope. The expandable cuff is moveable from a contracted configuration to a deployed configuration. The expandable cuff can be sized to press against the inner surface of a blood vessel or heart chamber when the expandable cuff is in the deployed configuration.

Figure 7:
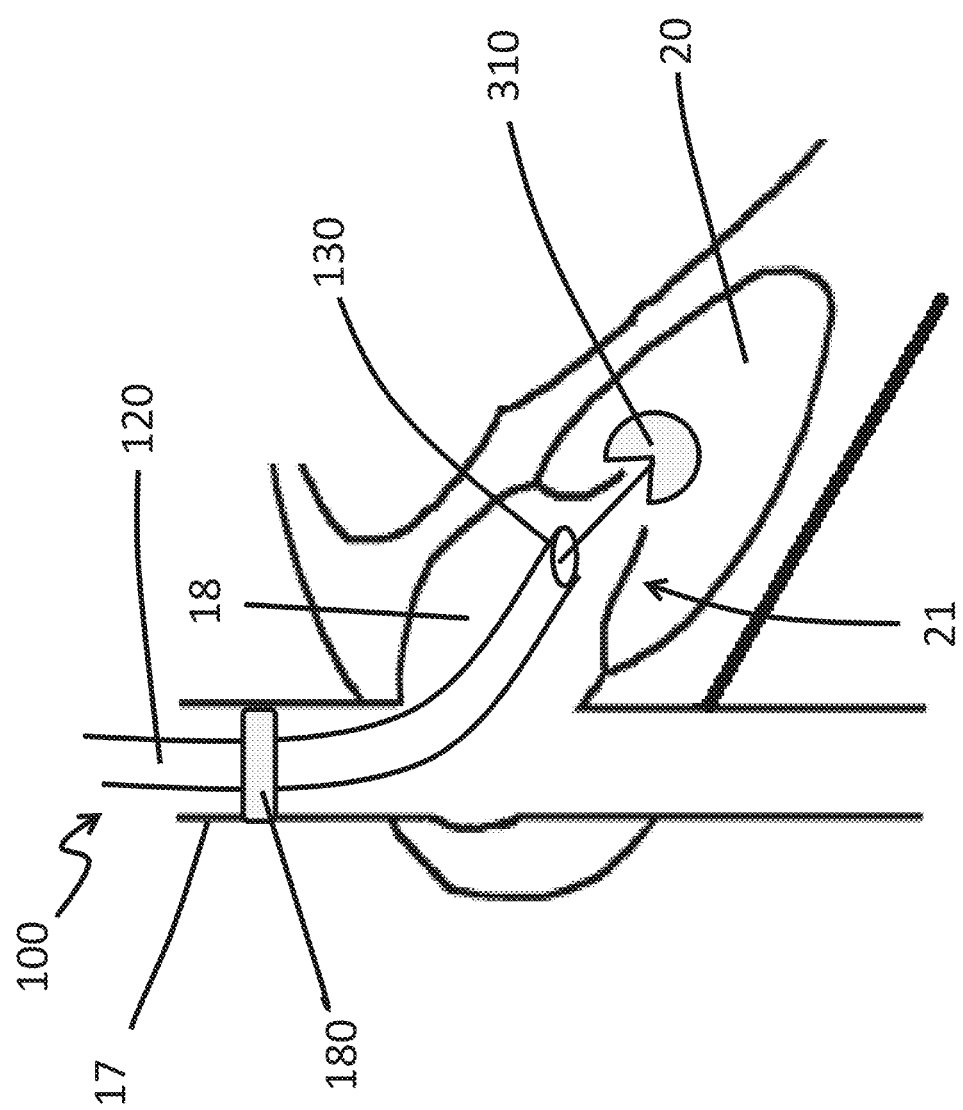
FIG. 7 is a schematic illustration of a use of an endoscope of the present disclosure to perform a medical procedure on a tricuspid valve of a heart in accordance with some embodiments herein.

FIG. 7 illustrates a method of using the endoscope 100 to perform a medical procedure. In the illustrated embodiment, the distal tip 130 of the endoscope 100 is advanced anterograde along the superior vena cava 17 and into the right atrium 18 of a heart 19. A heart-valve-leaflet capture device 310 (e.g., a clip) is deployed from the distal tip 130 and advanced into the right ventricle 20 to position the heart-valve-leaflet capture device 310 for capture of the leaflets of the tricuspid valve 21. The illustrated endoscope 100 has an expandable cuff 180 sized to press against the inner surface of the superior vena cava 17 when the expandable cuff 180 is in the deployed configuration. As discussed herein, the expandable cuff 180 can stabilize or immobilize the position of the distal tip 130. The expandable cuff 180 can be moved into the deployed configuration to stabilize or immobilize the distal tip 130 while the heart-valve-leaflet device 310 is deployed from the distal tip 130. In some embodiments, the medical procedure comprises advancing the endoscope 100 through the aorta or via a puncture of the heart apex instead of the superior vena cava 17.

Example 2

An endoscopy system for performing a medical imaging procedure includes a hollow shaft comprising an expandable cuff disposed on an outer surface of the shaft, an image sensor and an illuminating element being disposed within the hollow shaft. The expandable cuff is moveable from a contracted configuration to a deployed configuration. The expandable cuff can be sized to occupy all or substantially all of an interior area of a cross section of the a blood vessel or other tube-like organ (e.g., intestine) when the expandable cuff is in the deployed configuration, thus inhibiting, reducing, or preventing fluid flow in the organ.

FIGS. 8A and 8B illustrate a method of using the endoscope 100 to perform a medical imaging procedure. In the illustrated embodiment, the distal tip 130 of the endoscope 100 is advanced along a vessel 4 (e.g., blood vessel) toward a target location 6. The target location 6 can be a region of surrounding tissue that is desired to be imaged. The distal tip 130 can have an opening that allows an image sensor within the endoscope 100 to image the field of view 8 as discussed herein. As shown in FIG. 8A, the expandable cuff 180 can be in the contracted configuration as the endoscope 100 is advanced toward the target location 6 to bring the target location 6 within the field of view 8 of the endoscope. FIG. 8B illustrates that once the endoscope 100 is properly positioned to view the target location 6, the expandable cuff 180 can be moved into the deployed configuration occupy substantially all of an interior area of a cross section the vessel 4 as discussed herein. When in the deployed configuration the expandable cuff 180 (in combination with the shaft 120) can inhibit, reduce, or prevent the flow of fluid in the vessel (e.g., blood in a blood vessel). The inhibition, reduction, or prevention of fluid downstream of the expandable cuff can permit imaging direct imaging of inside the vessel by the image sensor 140 in the distal tip 130 of the endoscope. After the imaging procedure is complete, the expandable cuff 180 can be moved to the contracted configuration, as discussed herein, and the endoscope 100 can be withdrawn from the vessel 4.

One skilled in the art will appreciate that, for processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. For example, "about 5", shall include the number 5. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

For methods disclosed herein, such as methods of performing a procedure, corresponding uses are also expressly contemplated. For example, for methods of performing a procedure (such as imaging) with an endoscope and/or endoscopy system, corresponding uses of the subject endoscopy system or endoscope for the procedure (such as imaging) are also contemplated.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

EXAMPLE EMBODIMENTS

The following example embodiments identify some possible permutations of combinations of features disclosed herein, although other permutations of combinations of features are also possible.

Example Embodiments

1. An microendoscope comprising
   a hub;
   a shaft extending from the hub and comprising a distal tip;
   an image sensor within the distal tip, the image sensor having a field of view external from the microendoscope;
   an illuminating element within the distal tip, the illuminating element configured to emit light within the field of view of the image sensor; and
   an expandable cuff disposed on at least a portion of the shaft, the expandable cuff being movable between a contracted configuration and a deployed configuration, an outer surface of the expandable cuff being disposed further away from a longitudinal axis of the shaft when the expandable cuff is in the deployed configuration than when the expandable cuff is in the contracted configuration.

2. The microendoscope of Embodiment 1, wherein the microendoscope is configured for use in a specified vessel, and wherein the expandable cuff, when expanded, has an outer diameter that is about the same as an inner diameter of the specified vessel.

3. The microendoscope of Embodiment 2, wherein the expandable cuff, when expanded, inhibits fluid flow in the specified vessel, such as blood flow, thereby permitting visualization of an interior of the vessel by the image sensor.

4. The microendoscope of any one of Embodiments 2-3, wherein the specified vessel is selected from the group consisting of: a femoral artery, a radial artery, a pulmonary vein, a coronary artery, an aorta, and a carotid artery.

5. The microendoscope of any one of the preceding Embodiments, wherein the expandable cuff is a radially-expandable sleeve or protrusion.

6. The microendoscope of any one of the preceding Embodiments, wherein the expandable cuff further comprises a internal space in fluid communication with an inflation port disposed on the hub.

7. The microendoscope of Embodiment 6, wherein the expandable cuff in the contracted configuration adopts the deployed configuration when a fluid or gas is introduced into the internal space through the inflation port.

8. The microendoscope of any one of the preceding Embodiments, further comprising:
   a working channel disposed within the shaft and extending from the hub to the distal tip, at least a portion of the working channel being disposed between the longitudinal axis of the shaft and an overlying portion of the expandable cuff.

9. The microendoscope of Embodiment 8, wherein the overlying portion of the expandable cuff comprises an inner surface disposed between the working channel and the internal space of the expandable cuff, the inner surface being less distensible than the outer surface.

10. The microendoscope of any one of the preceding Embodiments, wherein the expandable cuff comprises two or more portions circumferentially disposed around the shaft.

11. The microendoscope of any one of the preceding Embodiments, wherein the internal space of the expandable cuff comprises a plurality of inflation channels, each of the plurality of inflation channels being fluidically isolated from one another.

12. The microendoscope of any one of Embodiments 1-11, further comprising a mitral clip, wherein the specified vessel is selected from the group consisting of: the inferior vena cava and the aorta.

13. The microendoscope of any one of Embodiments 1-11, wherein the microendoscope is configured to ablate the pulmonary vein using electrocautery or cryotherapy.

14. The microendoscope of any one of the preceding Embodiments, wherein the expandable cuff is configured for percutaneous access to the specified vessel.

15. The microendoscope of any one of the preceding Embodiments, wherein the expandable cuff has a longitudinal length of at least about 2 centimeters.

16. The microendoscope of Embodiment 1, wherein the microendoscope in the contracted configuration is configured to ride along a guidewire through a blood vessel 17. The microendoscope of Embodiment 1 or 16, wherein the microendoscope further comprises a guidewire lumen sized to receive a guidewire.

18. The microendoscope of Embodiment 17, further comprising a working channel disposed within the shaft and extending from the hub to the distal tip, at least a portion of the working channel being disposed between the longitudinal axis of the shaft and an overlying portion of the expandable cuff, the working channel comprising the guidewire lumen.

19. The microendoscope of Embodiment 17 or 18, wherein the microendoscope is configured to enter the deployed configuration while the guidewire is disposed in the guidewire lumen.

20. The microendoscope any one of Embodiments 17-19, wherein a proximal end of the guidewire lumen is disposed on the hub.

21. A method of using an expandable microendoscope, the method comprising:
   advancing the expandable microendoscope within a vessel to a target location; and expanding an expandable cuff of the microendoscope so that an outer surface of the expandable cuff contacts two or more portions of an inner surface of the vessel, wherein the portions are circumferentially disposed around the microendoscope.

22. The method of Embodiment 21, wherein the expandable cuff contacting the portions of the inner surface of the vessel maintains a position of the expandable microendoscope within the vessel.

23. The method of any one of Embodiments 21-22 wherein the expandable cuff contacting the portions of the inner surface of the vessel inhibits fluid flow in the vessel, thereby permitting visualization of an interior of the vessel.

24. The method of any one of Embodiments 21-23, wherein expanding the expandable cuff comprises introducing a fluid into an internal space of the expandable cuff.

25. The method of any one of Embodiments 21-24, wherein the vessel is selected from the group consisting of the femoral artery, radial artery, superior vena cava, aorta, and pulmonary vein 26. The method of any one of Embodiments 21-25, wherein the target location is selected from the group consisting of a heart, a brain, a leg, a foot, an ankle, an arm, or a hand.

27. The method of any one of Embodiments 21-26, wherein the target location comprises a peripheral artery, and wherein the vessel is the peripheral artery.

28. The method of any one of Embodiments 21-27 further comprising:
deploying an instrument from a working channel of the expandable microendoscope, wherein at least a portion of the working channel passes between the expandable cuff and a longitudinal axis of the expandable microendoscope.

29. The method of Embodiment 28 wherein deploying the instrument comprises distending an inner surface of the expandable cuff with an outer surface of the working channel.

30. The method of any one of Embodiments 28-29, wherein the instrument comprises a mitral clip.

31. The method of Embodiment 30, wherein the vessel is selected from the group consisting of the inferior vena cava and the aorta.

32. The method of Embodiment 30, wherein the target location comprises the heart, and wherein the vessel is the inferior vena cava, the method further comprising visualizing tissue of the heart while the expandable cuff is expanded in the inferior vena cava, wherein the mitral clip is applied to the heart after the visualizing.

33. The method of any one of Embodiments 28-30, wherein the instrument ablates a portion of a pulmonary vein.

34. The method of any one of Embodiments 21-33, further comprising collecting images distal to a leading end of the microendoscope while the position of the microendoscope is maintained.

35. The method of Embodiment 21, wherein advancing comprises moving the expandable microendoscope along a guidewire toward the target location.

36. The method of Embodiment 35, wherein advancing further comprises:
halting the expandable microendoscope along the guidewire;
expanding the expandable cuff, whereby the expanded expandable cuff blocks blood flow in the vessel;
imaging a field of view in the vessel while the blood flow is blocked;
contracting the expandable cuff; and
resuming moving the expandable microendoscope toward the target location along the guidewire.

37. The method of Embodiment 36, wherein the vessel is the radial artery or femoral artery.

38. The method of Embodiment 36, wherein the vessel is the coronary artery, and the target location comprises a portion of the coronary artery comprising an obstruction 39. An endoscopy system comprising:
an microendoscope comprising an image sensor disposed within a distal tip of the microendoscope, an illuminating element within the distal tip, and an expandable cuff disposed on an outer surface of the microendoscope;
a guidewire sized to pass through a lumen of the expandable microendoscope; and
an inflation pump in fluid communication with an internal space of the expandable cuff.

40. The endoscopy system of Embodiment 30, wherein the microendoscope comprises, consists essentially of, or consists of the microendoscope of any one of Embodiments 1-15

Some embodiments include a method of using an endoscope, for example an endoscope as described herein. In some embodiments, the method includes advancing the expandable endoscope within a vessel to a target location, expanding an expandable cuff of the endoscope to bring an outer surface of the expandable cuff into contact with two or more portions of an inner surface of the vessel, the two or more portions being circumferentially disposed around the endoscope. Bringing the expandable cuff into contact with portions of the inner surface of the vessel can inhibit, reduce, or stop fluid flow in the vessel (such as blood flow in the blood vessel), thus permitting visualization of the interior of the vessel. The visualization can be performed by an image sensor as described herein. In some embodiments, expanding the expandable cuff includes introducing a fluid into an internal space of the expandable cuff. In some embodiments, bringing the expandable cuff into contact with portions of the inner surface of the vessel maintains a position of the expandable endoscope within the vessel. In some embodiments, the method further includes deploying an instrument from a working channel of the expandable endoscope, wherein at least a portion of the working channel passes between the expandable cuff and a longitudinal axis of the expandable endoscope. In some embodiments, deploying the instrument includes distending an inner surface of the expandable cuff with an outer surface of the working channel. In some embodiments, the method includes deploying a mitral clip from the working channel. In some embodiments, the method includes deploying from the working channel an instrument that is adapted to ablate a portion of a pulmonary vein. In some embodiments, the method further comprises collecting images distal to a leading end of the endoscope while the position of the endoscope is maintained.

What is claimed is:
1. A method of imaging an interior of a vessel, the method comprising:
advancing an endoscope within a vessel to a target location, the endoscope comprising:
a hub;
a shaft extending from the hub and comprising a distal tip;
an image sensor within the distal tip, the image sensor having a field of view external from the endoscope;
an expandable cuff disposed on at least a portion of the shaft, the expandable cuff being movable between a contracted configuration and a deployed configuration, an outer surface of the expandable cuff being disposed further away from a longitudinal axis of the shaft when the expandable cuff is in the deployed configuration than when the expandable cuff is in the contracted configuration; and a working channel;

expanding the expandable cuff to the deployed configuration so that the expandable cuff and at least the portion of the shaft occupy all or substantially all of an interior area of a cross section of the vessel, whereby fluid flow is inhibited, reduced, or prevented in the vessel at the target location;

collecting an image of the interior of the vessel at the target location while the fluid flow is inhibited, wherein the image is sensed by the image sensor; and deploying an instrument from the working channel of the endoscope, wherein at least a portion of the working channel passes between the expandable cuff and a longitudinal axis of the endoscope, wherein deploying the instrument comprises distending an inner surface of the expandable cuff with an outer surface of the working channel.

2. The method of claim 1, wherein inhibiting fluid flow in the vessel permits visualization of the interior of the vessel.

3. The method of claim 1, wherein the vessel is selected from the group consisting of a femoral artery, a radial artery, a superior vena cava, an aorta, a carotid artery, a coronary artery, and a pulmonary vein.

4. The method of claim 1, wherein the target location is selected from the group consisting of a heart, a brain, a leg, a foot, an ankle, an arm, or a hand.

5. The method of claim 1, wherein the instrument comprises a mitral clip.

6. The method of claim 5, wherein the vessel is selected from the group consisting of an inferior vena cava and an aorta.

7. The method of claim 6, wherein the target location comprises a heart, and wherein the vessel is the inferior vena cava, the method further comprising visualizing tissue of the heart while the expandable cuff is expanded in the inferior vena cava, wherein the mitral clip is applied to the heart after the visualizing.

8. The method of claim 1, wherein the instrument ablates a portion of a pulmonary vein.

9. The method of claim 1, the endoscope further comprising an illuminating element within the distal tip, the illuminating element configured to emit light within a field of view of the image sensor, the method further comprising illuminating the interior of the vessel at the target location.

10. The method of claim 1, wherein advancing comprises moving the endoscope along a guidewire toward the target location.

11. The method of claim 10, wherein the vessel is a blood vessel, wherein advancing further comprises:

halting the endoscope along the guidewire;

expanding the expandable cuff to the deployed configuration, whereby the deployed expandable cuff and shaft inhibit, reduce, or prevent blood flow in the vessel;

imaging a field of view in the vessel while the blood flow is inhibited, reduced, or prevented;

contracting the expandable cuff; and resuming moving the endoscope toward the target location along the guidewire.

12. The method of claim 11, wherein the vessel is a radial artery or a femoral artery.

13. The method of claim 11, wherein the vessel is a coronary artery, and the target location comprises a portion of the coronary artery comprising an obstruction.

* * * * *